US011010797B2

(12) United States Patent
Dow et al.

(10) Patent No.: US 11,010,797 B2
(45) Date of Patent: May 18, 2021

(54) SENSORS AND SENTIMENT ANALYSIS FOR RATING SYSTEMS

(71) Applicant: International Business Machines Corporation, Armonk, NY (US)

(72) Inventors: Eli M. Dow, Wappingers Falls, NY (US); Yunli Tang, Poughkeepsie, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 88 days.

(21) Appl. No.: 15/641,763

(22) Filed: Jul. 5, 2017

(65) Prior Publication Data

US 2019/0012709 A1 Jan. 10, 2019

(51) Int. Cl.
| | |
|---|---|
| *G06Q 30/02* | (2012.01) |
| *A61B 5/024* | (2006.01) |
| *A61B 5/00* | (2006.01) |
| *A61B 5/16* | (2006.01) |
| *A61B 5/08* | (2006.01) |

(Continued)

(52) U.S. Cl.
CPC ....... *G06Q 30/0282* (2013.01); *A61B 5/0022* (2013.01); *A61B 5/02438* (2013.01); *A61B 5/165* (2013.01); *A61B 5/7278* (2013.01); *G06Q 30/0201* (2013.01); *A61B 5/021* (2013.01); *A61B 5/0531* (2013.01); *A61B 5/0816* (2013.01); *G06Q 30/0203* (2013.01); *G06Q 30/0261* (2013.01)

(58) Field of Classification Search
CPC ................................................ G06Q 30/0282
See application file for complete search history.

(56) References Cited

U.S. PATENT DOCUMENTS 9,202,233 B1 12/2015 Siegel et al.
10,271,099 B2 4/2019 Dey et al.
(Continued)

FOREIGN PATENT DOCUMENTS

| WO | 2013012211 A2 | 1/2013 |
| WO | 2013033385 A1 | 3/2013 |
| WO | 2015106287 A1 | 7/2015 |

OTHER PUBLICATIONS

"Wearing Your Intelligence: How to Apply Artificial Intelligence," Wired, Dec. 4, 2014, available online at https://www.wired.com/insights/2014/12/wearing-your-intelligence/ (Year: 2014).*

(Continued)

*Primary Examiner* — Jan P Mincarelli
(74) *Attorney, Agent, or Firm* — Cantor Colburn LLP; Teddi Maranzano

(57) ABSTRACT

A processor-implemented method for analyzing sentiment data corresponding to users experiencing an entertainment to generate a sentiment rating is provided. The processor-implemented method includes collecting physical data procured by wearable devices corresponding to the users during the entertainment. The processor-implemented method includes analyzing the physical data to determine sentiment data and generating the sentiment rating for the entertainment based on the sentiment data. The sentiment rating quantifies a collective real-time emotional response for the users that experience the entertainment.

13 Claims, 4 Drawing Sheets

(51) Int. Cl.
    *A61B 5/0531*    (2021.01)
    *A61B 5/021*    (2006.01)

(56) References Cited

U.S. PATENT DOCUMENTS

| | | | |
|---|---|---|---|
| 2005/0289582 A1* | 12/2005 | Tavares | G06K 9/00221 |
| | | | 725/10 |
| 2008/0065468 A1 | 3/2008 | Berg et al. | |
| 2012/0290910 A1 | 11/2012 | Kumar | |
| 2012/0324494 A1 | 12/2012 | Burger et al. | |
| 2013/0091214 A1 | 4/2013 | Kellerman et al. | |
| 2013/0245396 A1 | 9/2013 | Berman et al. | |
| 2014/0347265 A1 | 11/2014 | Aimone et al. | |
| 2015/0148071 A1* | 5/2015 | Elmore | H04W 4/023 |
| | | | 455/456.2 |
| 2015/0347903 A1* | 12/2015 | Saxena | G06T 11/206 |
| | | | 706/11 |
| 2016/0007083 A1 | 1/2016 | Gurha | |
| 2016/0021425 A1 | 1/2016 | Eriksson et al. | |
| 2016/0055236 A1 | 2/2016 | Frank | |
| 2016/0055430 A1* | 2/2016 | Naji | G06Q 50/01 |
| | | | 705/5 |
| 2016/0148122 A1* | 5/2016 | Paleja | G06Q 10/02 |
| | | | 705/5 |
| 2016/0170996 A1 | 6/2016 | Frank et al. | |
| 2016/0205431 A1* | 7/2016 | Avedissian | H04N 21/8456 |
| | | | 725/37 |
| 2016/0212466 A1 | 7/2016 | Nauseef et al. | |
| 2016/0226610 A1* | 8/2016 | Pinzon Gonzales, Jr. | |
| | | | H04N 21/4667 |
| 2018/0053197 A1 | 2/2018 | Chan et al. | |
| 2018/0260825 A1* | 9/2018 | Rashid | G06Q 30/0201 |
| 2018/0276710 A1* | 9/2018 | Tietzen | G06N 3/08 |

OTHER PUBLICATIONS

List of IBM Patents or Patent Applications Treated as Related; (Appendix P), Filed Nov. 13, 2017, 2 pages.

Eli M. Dow et al., "Sensors and Sentiment Analysis for Rating Systems ", U.S. Appl. No. 15/810,328, filed Nov. 13, 2017.

De Albornoz, Jorge Carrillo, et al. "A joint model of feature mining and sentiment analysis for product review rating." EuropeanConferenceonInformation Retrieval.Springer2011.

* cited by examiner

SENSORS AND SENTIMENT ANALYSIS FOR RATING SYSTEMS

BACKGROUND

The present invention relates to sensor and sentiment analysis for rating systems.

In general, conventional rating systems rate or output ratings for entertainment, such as films, movies, television shows, concerts, performances, shows, plays, and the like. The ratings are intended to quantify popular opinion of the entertainment so that individuals, businesses, and/or companies can utilize corresponding ratings to make decisions with respect to the entertainment (e.g., whether to attend a play, associate advertisements during movie previews, change the cost of admission to a concert, etc.). However, because conventional rating systems do not capture an accurate depiction of how a user feels while experiencing the entertainment, the individuals, the businesses, and/or the companies may be making misinformed decisions.

For instance, users that rate a movie are typically users who are on an extreme (e.g., either hate or love the movie). In other cases, users may rate the movie for a reason beyond the movie itself (e.g., the lead actor is a favorite, the popcorn was exceptional, etc.). In addition, users may delay in rating the movie, which can open their opinions to outside influences and changes. Ultimately, the rating for the movie is a skewed or wrong result with respect to a true sentiment rating.

SUMMARY

In accordance with one or more embodiments, a processor-implemented method for analyzing sentiment data corresponding to users experiencing an entertainment to generate a sentiment rating is provided. The processor-implemented method includes collecting physical data procured by wearable devices corresponding to the users during the entertainment. The processor-implemented method includes analyzing the physical data to determine sentiment data and generating the sentiment rating for the entertainment based on the sentiment data. The sentiment rating quantifies a collective real-time emotional response for the users that experience the entertainment.

Embodiments of the present invention can also include the above processor-implemented method implemented as a system and/or a computer program product.

Additional features and advantages are realized through the techniques of the present disclosure. Other embodiments and aspects of the disclosure are described in detail herein. For a better understanding of the disclosure with the advantages and the features, refer to the description and to the drawings.

DETAILED DESCRIPTION

In view of the above, embodiments disclosed herein may include system, method, and/or computer program product (herein a sensor and sentiment analysis system) that analyzes sentiments of users experiencing any entertainment to generate a sentiment rating. Technical effects and benefits of the sensor and sentiment analysis system include generating a sentiment rating that quantifies a collective real-time emotional response for the users that experience entertainment. Thus, embodiments described herein are necessarily rooted in sensor and sentiment analysis system to perform proactive operations to overcome problems specifically arising with conventional rating systems.

Figure 1:
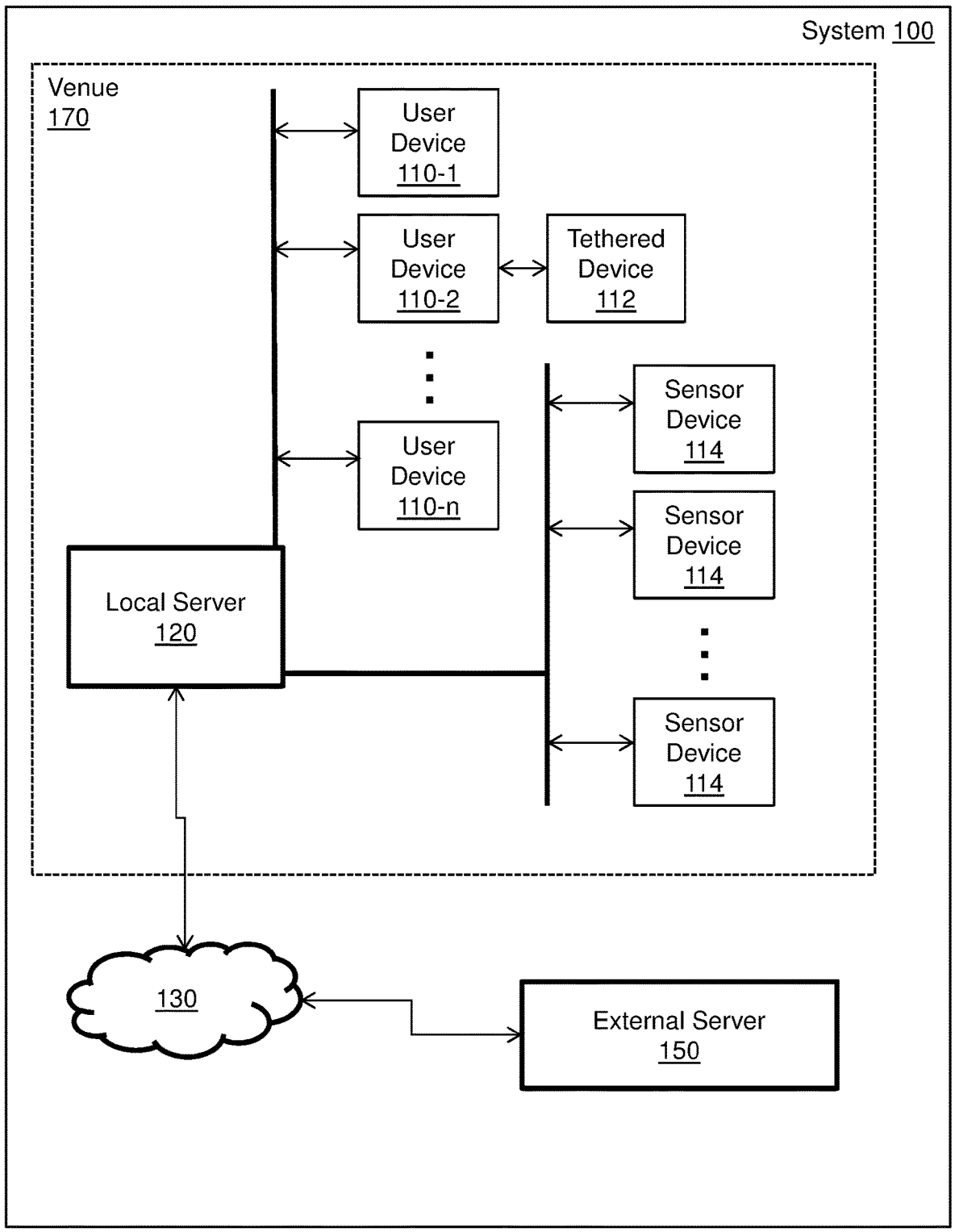
FIG. 1 depicts a system in accordance with one or more embodiments.

Turning now to FIG. 1, a system 100 is shown as an example of the sensor and sentiment analysis system in accordance with an embodiment. The system 100 comprises one or more user devices 110 (e.g., 110-1, 110-2, . . . , 110-n), at least one tethered device 112, one or more sensor devices 114, a local server 120, a network 130, and an external server 150.

The system 100 can be an electronic, computer framework comprising and/or employing any number and combination of computing devices and networks utilizing various communication technologies. The system 100 can be easily scalable, extensible, and modular, with the ability to change to different services or reconfigure some features independently of others.

The one or more user devices 110, the at least one tethered device 112, the one or more sensor devices 114, and the local server 120 are located within a venue 170, which represents and/or comprises a local network. The local server 120 connects to the external server 150, which is not located within the venue 170 via the network 130. The local network and/or the external network 130 can utilize a plurality of communication technologies, such as radio technologies, cellular technologies, etc., to transmit communications between the local server 120 and the external server 150. Examples of the network 130 include, but are not limited to, the Internet, a local area network, a wide area network and/or a wireless network.

Each of the one or more user devices 110, the at least one tethered device 112, the one or more sensor devices 114, the local server 120, and the external server 150 can be a computing device with a processor and a memory configured to receive and respond to electrical communications. Further, the arrows of FIG. 1 represent the electrical communications between the elements for FIG. 1. Note that the thick lines extending from the local server 120 represent one or more communication interfaces of the local network through which the one or more user devices 110, the at least one tethered device 112, and/or the one or more sensor devices 114 communicatively connect to the local server 120).

The one or more user devices 110, the at least one tethered device 112, and the one or more sensor devices 114 can generally be referred to as mobile devices. A mobile device is a portable computing device comprising at least a processor and a memory. Examples of a mobile device include smartphones, tablet computers, personal digital assistants, wearable devices (e.g., watches), etc. Mobile devices can include one or more sensors for detecting physical data or can connect to other devices including the same. A sensor can comprise any electro-mechanical device for detecting conditions of an object or environment (sensor examples include biometric detectors, such as pulse sensors, moisture detectors, heat sensors, etc.).

In operation, the system 100 utilizes can utilize one or more sensors (e.g., the one or more sensor devices 114 and/or the at least one tethered device 112) to capture physical data of one or more users at the venue 170 experiencing entertainment. The system 100 utilizes can also utilize mobile devices (e.g., the one or more user devices 110) to receive user inputs from the one or more users. The system 100 can capture the physical data and/or the user inputs during the entertainment in real-time or immediately after experiencing the entertainment.

The physical data can comprise sensor readings that capture and identify a status of bodily functions (i.e., blood pressure, heart rate, breathing rates, and skin conductance) of the one or more users. The user inputs can comprise direct feedback for information submitted by the one or more users via corresponding mobile devices. Note that 'immediately after experiencing the entertainment' can be defined as a time interval beginning at a conclusion of the entertainment and extending for a predetermined amount of time. In accordance with one or more embodiments, the predetermined amount of time can be chosen from a range of one second to one day.

For example, as shown in FIG. 1, the user device 110-1 and the one or more sensor devices 114 can be standalone mobile devices capable of detecting/receiving physical data, and the user device 110-2 can be coupled to the at least one tethered device 112 that also detects/receives physical data. In a first user device 110-1 case, a biometric scanner can be included in the user device 110-1 to determine a pulse of a user. In a second user device 110-2 case, the tethered device 112 can be a wearable device that includes a biometric scanner to determine a pulse of a user, which is then transmitted to the user device 110-2. In both cases, the user devices 110-1 and 110-2 can transmit the pulse, as physical data, to the local server 120. In the sensor device 114 case, the sensor is a wearable device that automatically transmits physical data (i.e., the pulse of a user) to the local server 120.

The system 100 analyzes the physical data and/or the user inputs to determine sentiment data for each of the one or more users. The sentiment data quantifies how a user feels (i.e., a sentimental or emotional response) with respect to the entertainment. The system 100 utilizes can utilize the sentiment data (for each of the one or more users who experience the entertainment) to compile a sentiment rating for the entertainment. The sentiment rating is a value that assesses and quantifies a user emotional response for a user population that experiences the entertainment.

With respect to system 100, the local server 120 and/or the external server 150 can analyze the physical data and/or the user inputs to determine the sentiment data and utilize the sentiment data to compile a sentiment rating for the entertainment. The local server 120 and the external server 150 can also comprise a database, data repository or other data store and may include various kinds of mechanisms for storing, accessing, retrieving, and processing various kinds of data (e.g., the physical data, the user inputs, the sentiment data, and the sentiment rating), including a hierarchical database, a set of files in a file system, an application database in a proprietary format, a relational database management system (RDBMS), etc.

Figure 2:
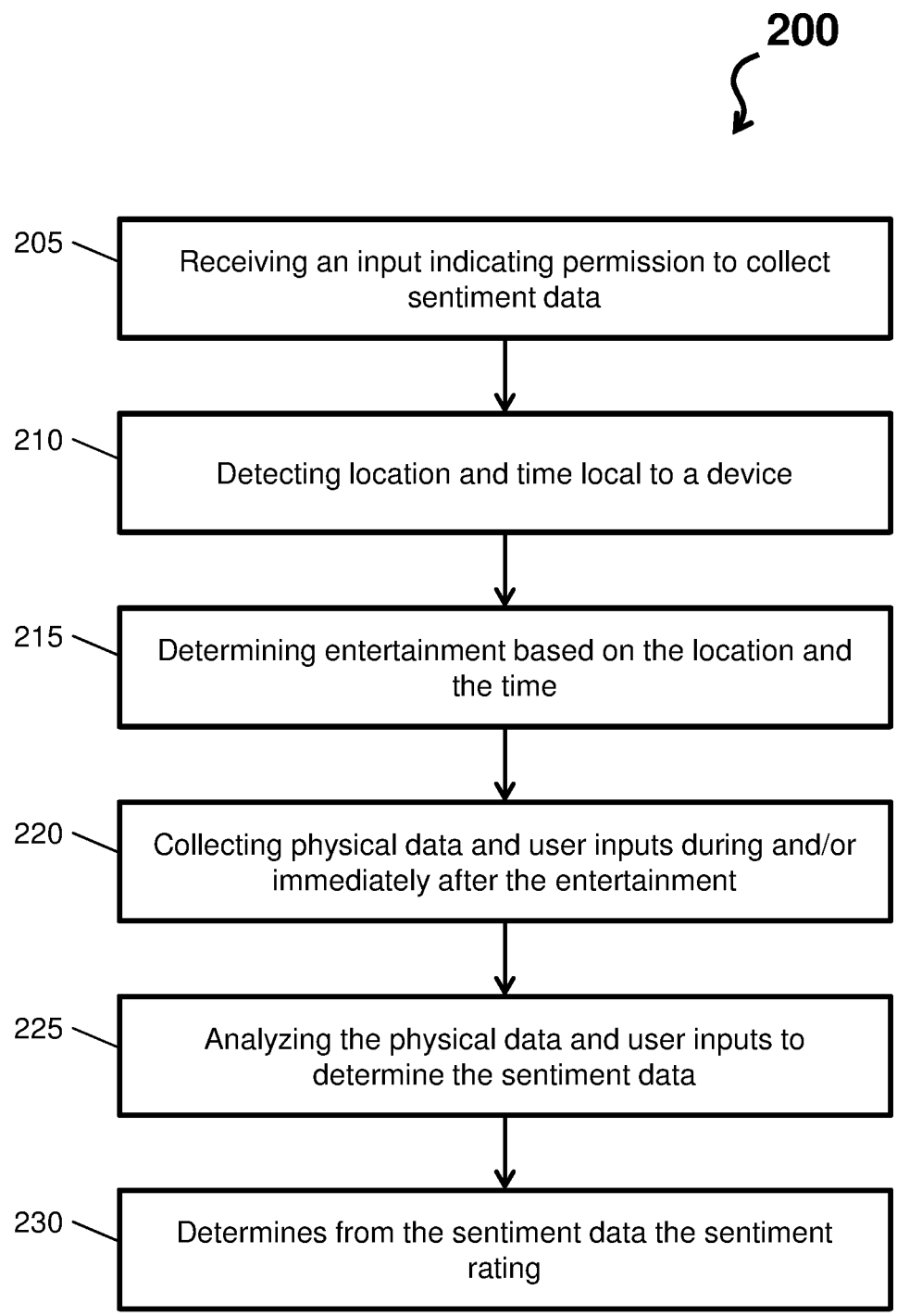
FIG. 2 depicts a process flow of system in accordance with one or more embodiments.

Turning now to FIG. 2, an operational embodiment of the system 100 of FIG. 1 is described with respect to the process flow 200 in accordance with one or more embodiments. In general, the process flow 200 analyzes sentiments of users experiencing any entertainment to generate the sentiment rating.

The process flow 200 begins at block 205, where the system 100 receives an input indicating permission to collect sentiment data. The input indicating permission is representative of one or more inputs, each of which is provided by a user via their corresponding mobile device, identifying that a user has optioned-into (opted-in) participating in the collection of the sentiment data. The receipt of an input indicating permission by the system 100 can include receiving permission at the one or more mobile devices 110, the local server 120, and/or the external server 150.

The system 100 can incentivize the one or more users to provide both the physical data and the user inputs. For instance, if watching a movie, the system 100 can indicate to the user that they can receive a discounted movie ticket if the user grants permission to the system 100 to obtain physical data from sensors contained within their wearables and to provide a few words at an end of the movie discussing their thoughts of the movie via their mobile devices.

At block 210, the system 100 detects a location and time local to a mobile device. The location and the local time are detected for each mobile device that has provided the input indicated permission to collect sentiment data. The location can be determined utilizing location services of the mobile device and/or by the mobile device being on a local network of the venue 170. The time local can be determined by the clock of the mobile device. The detection of the location and the local time by the system 100 can be performed by the one or more mobile devices 110, the local server 120, and/or the external server 150.

At block 215, the system 100 determines an entertainment based on the location and the time. The system 100 can confirm that a user is at a specific location at a particular time with respect to the entertainment to verify that the user is actually experiencing the entertainment. The system 100 can compare the specific location and time to a schedule for the venue 117 already in the local server 120. For example, the system 100 can utilize the local network of the venue 170 to determine that the user device 110-1 is on the premises. In the case of a movie theater, the local network can determine which theater room the mobile device is in, and therefore can determine based on time which movie the user is watching.

At block 220, the system 100 collects physical data and user inputs during and/or immediately after the entertainment. The system 100 can utilize the sensor devices 114, the tethered device 112, and the user devices 110 to receive the physical data and the user inputs.

At block 225, the system 100 analyzes the physical data and the user inputs to determine sentiment data. That is, the physical data and the user inputs are processed to generate the sentiment data for each user who opted-in. For example, each pulse of a user is used to determine whether a heart rate has accelerated or remained the same while experiencing the entertainment. If during a horror movie, the heart rates of the users increase during the horror movie, the system 100 determines that the sentiment of the users is scared/excited. The analyzation of the physical data and the user inputs by the system 100 can be performed by the one or more mobile devices 110, the local server 120, and/or the external server 150. The analyses of the physical data and the user inputs can include natural language processing, text analysis, computational linguistics, and biometrics to systematically identify, extract, quantify, and study affective states and subjective information to determine the sentiment data of the one or more users.

At block 230, the system 100 determines from the sentiment data the sentiment rating. For instance, using the sentiment data based on the collected physical data and user inputs, the system 100 determines the overall experience of the users. The sentiment rating is a value that assesses and quantifies a collective emotional response for users that experience the entertainment. The sentiment rating determination by the system 100 can be performed by the one or more mobile devices 110, the local server 120, and/or the external server 150.

Figure 3:
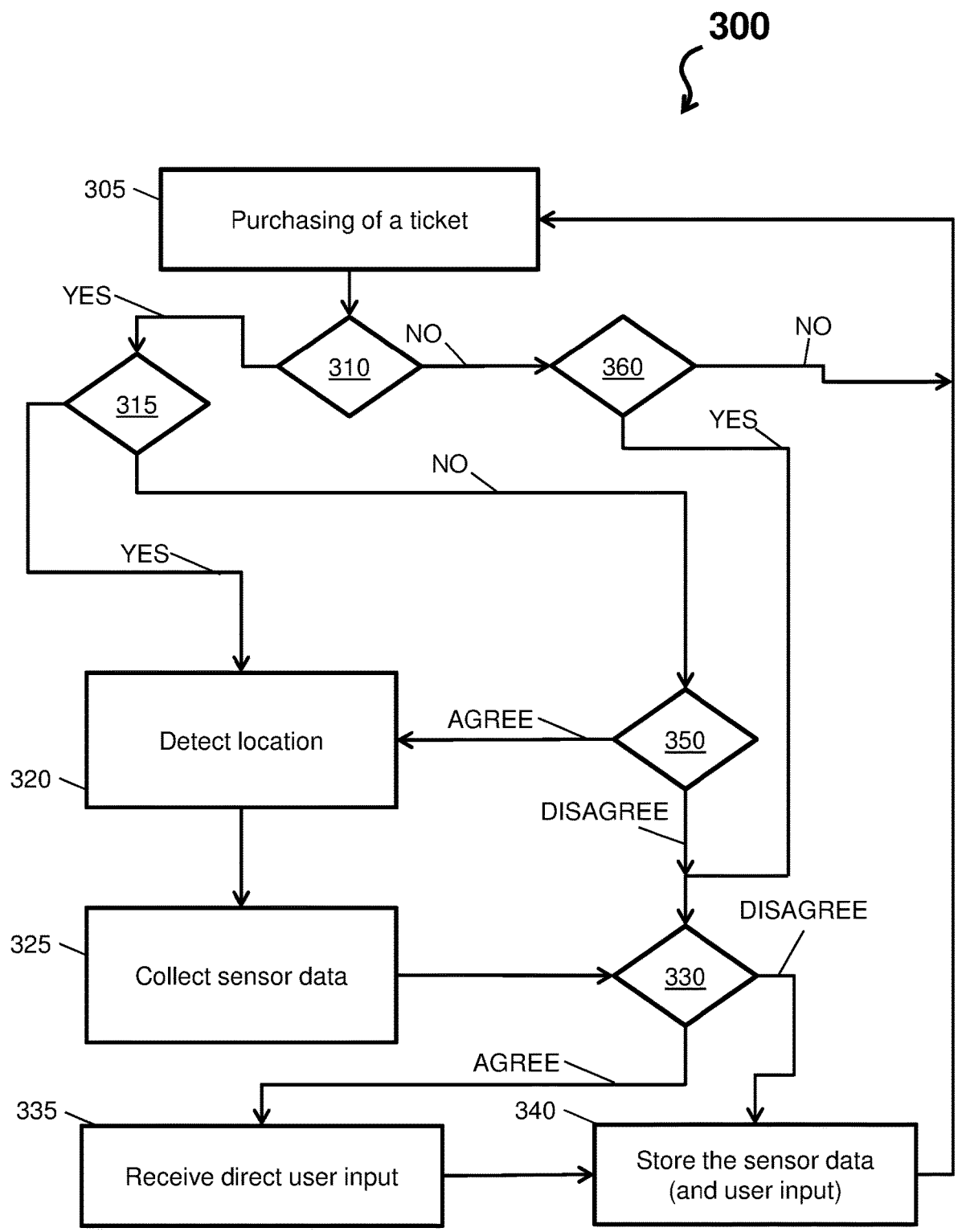
FIG. 3 depicts a process flow of system in accordance with one or more embodiments.

FIG. 3 depicts a process flow 300 of a sensor and sentiment analysis system in accordance with one or more embodiments. The process flow 300 begins at block 305, where a user purchases a ticket. For instance, the user arrives at an entertainment venue (e.g., a movie theater, a concert hall, etc.) and buys the ticket to experience an entertainment at the entertainment venue (e.g., the venue 170).

At decision block 310, the sensor and sentiment analysis system determines whether the user grants permission to access sensor information on a wearable device. The wearable device can be user provided or venue provided. For instance, upon buying the ticket at a kiosk, the user is proposed with an opportunity (via pop-up on the kiosk during the purchase) to allow the sensor and sentiment analysis system to access sensor information from the wearable device while the user experiences the entertainment. The user can also be proposed with an opportunity to provide thoughts after the entertainment. In return, the sensor and sentiment analysis system indicate that an incentive (i.e. 10% off next ticket, free popcorn, etc.) will be received by opting-in.

If the sensor and sentiment analysis system determine that the user has granted permission to access the sensor information on the wearable device, then the process flow 300 proceeds to decision block 315 via the YES arrow. For instance, at the kiosk, the user is proposed type in a ticket code (provided via the kiosk) into an application to sync the mobile phone with the sensor and sentiment analysis system. At decision block 315, the sensor and sentiment analysis system determines whether the user has an application on their mobile device (e.g., the application communicates with the sensor and sentiment analysis system in response to the ticket code being entered into the applications). If the sensor and sentiment analysis system determines that the user has the application on their mobile device, then the process flow 300 proceeds to block 320 via the YES arrow.

At block 320, the sensor and sentiment analysis system determines a location of the mobile device. For instance, the sensor and sentiment analysis system utilizes a global positioning system of the mobile device to detect a location. At block 325, the sensor and sentiment analysis system collects sensor data (e.g., physical data). The sensor and sentiment analysis system can collect the physical data once the entertainment starts. For instance, as the user watches/listens to the entertainment, the wearable device collects physical data from sensors every few minutes. The wearable device can provide the physical data, once collected, to the sensor and sentiment analysis system.

At decision block 330, the sensor and sentiment analysis system determines whether the user will input their thoughts about the entertainment. In accordance with one or more embodiments, when the entertainment is over, the user is prompted as to whether they want to take a few minutes to say how they felt about the entertainment. If the sensor and sentiment analysis system determines that the user agrees to input their thoughts about the entertainment, the process flow 300 proceeds to block 335 via the AGREE arrow.

In accordance with one or more embodiments, when the entertainment is over, the permission received at block 310 enables the sensor and sentiment analysis system to prompt the user to enter their user input. Thus, the process flow 300 proceeds to block 335.

At block 335, the user provides direct feedback. For instance, the user can speak into the mobile device, which utilizes speech to text technology to turn their thoughts into text.

At block 340, the sensor and sentiment analysis system stores the sensor data (and the user input if received). Note that if the sensor and sentiment analysis system determines that the user does not agree to input their thoughts about the entertainment at decision block 330, the process flow 300 proceeds directly to block 340 via the DISAGREE arrow. The process flow 300 can then return to block 305 after block 340 and repeat upon the purchasing of another ticket.

Returning to decision block 315, if the sensor and sentiment analysis system determines that the user does not have the application on their mobile device, then the process flow 300 proceeds to block 350 via the NO arrow. At decision block 350, the sensor and sentiment analysis system requests via the kiosk for the user to download the application. The sensor and sentiment analysis system also can confirm that the user has granted permission to access the sensor information on the wearable device. If the sensor and sentiment analysis system determines that the user agrees to both conditions, the process flow 300 proceeds to block 320 via the AGREE arrow and the process flow 300 proceeds accordingly. If the sensor and sentiment analysis system determines that the user agrees to download the application but does not confirm their previous permission, the process flow 300 proceeds to block 330 via the DISAGREE arrow and the process flow 300 proceeds accordingly. In this case, if a user never agrees to provide physical data, the user can still provide direct feedback about the entertainment.

Returning to decision block 310, if the sensor and sentiment analysis system determines that the user has not granted permission to access the sensor information on the wearable device, then the process flow 300 proceeds to decision block 360 via the NO arrow. At decision block 360, the sensor and sentiment analysis system determines whether the user has an application on their mobile device. If the sensor and sentiment analysis system determines that the user has the application on their mobile device, then the process flow 300 proceeds to block 330 via the YES arrow and the process flow 300 proceeds accordingly. If the sensor and sentiment analysis system determines that the user does not have the application on their mobile device, then the process flow 300 proceeds to block 305 via the NO arrow and the process flow 300 proceeds accordingly.

Figure 4:
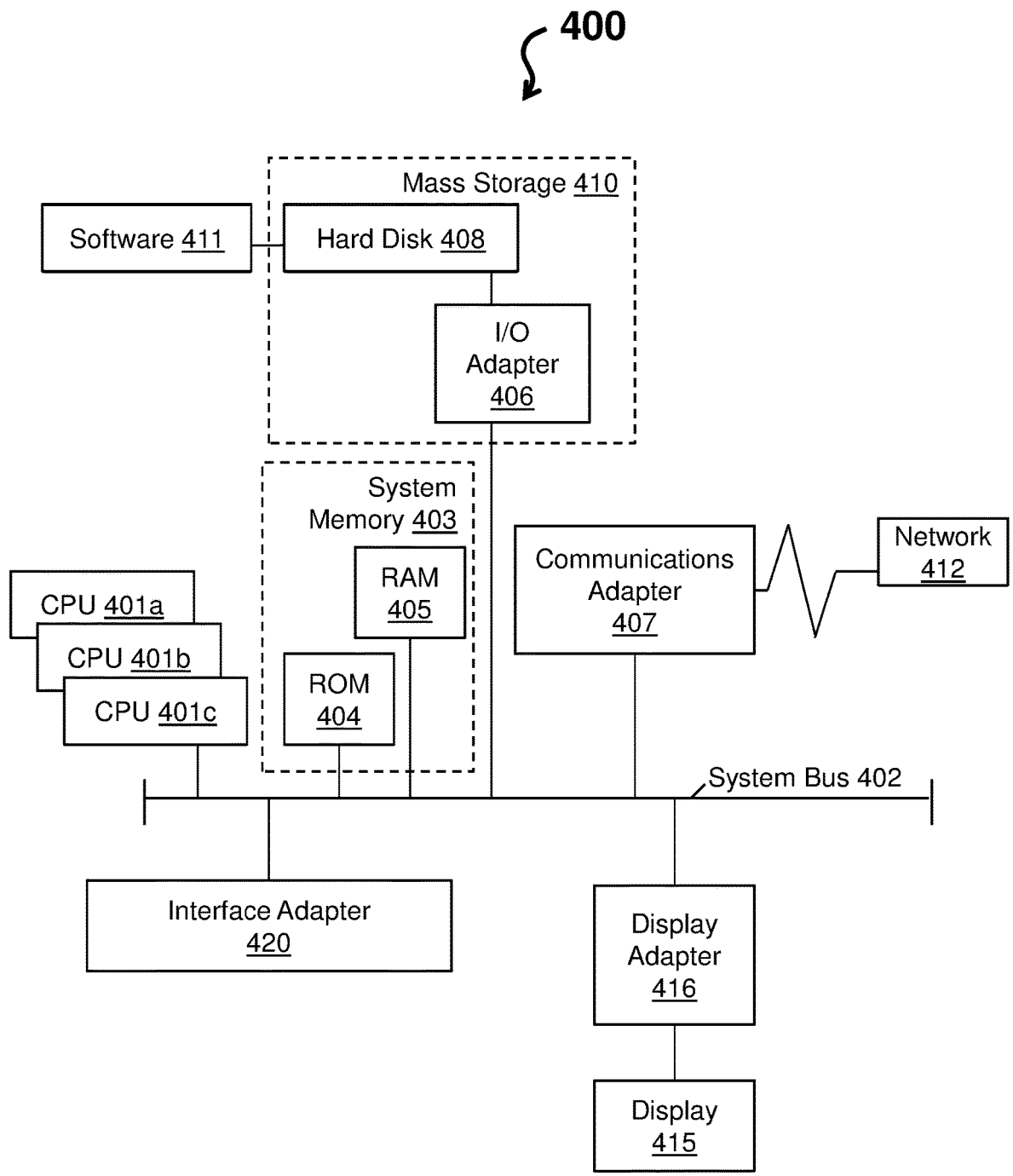
FIG. 4 depicts a processing system in accordance with one or more embodiments.

FIG. 4 depicts an example of a system 400 in accordance with one or more embodiments. The system 400 has one or more central processing units (CPU(s)) 401a, 401b, 401c, etc. (collectively or generically referred to as processor(s) 401). The processors 401, also referred to as processing circuits, are coupled via a system bus 402 to system memory 403 and various other components. The system memory 403 can include a read only memory (ROM) 404 and a random access memory (RAM) 405. The ROM 404 is coupled to the system bus 402 and may include a basic input/output system (BIOS), which controls certain basic functions of the system 400. The RAM is read-write memory coupled to the system bus 402 for use by the processors 401.

FIG. 4 further depicts an input/output (I/O) adapter 406 and a communications adapter 407 coupled to the system bus 402. The I/O adapter 406 may be a small computer system interface (SCSI) adapter that communicates with a hard disk 408 and/or any other similar component. The I/O adapter 406 and the hard disk 408 are collectively referred to herein as a mass storage 410. A software 411 for execution on the system 400 may be stored in the mass storage 410.

The mass storage 410 is an example of a tangible storage medium readable by the processors 401, where the software 411 is stored as instructions for execution by the processors 401 to cause the system 400 to operate, such as is described herein with reference to FIG. 2. Examples of computer program product and the execution of such instruction is discussed herein in more detail. Referring again to FIG. 4, a communications adapter 407 interconnects the system bus 402 with a network 412, which may be an outside network, enabling the system 400 to communicate with other such systems. A display (e.g., screen, a display monitor) 415 is connected to the system bus 402 by a display adapter 416, which may include a graphics controller to improve the performance of graphics intensive applications and a video controller. In one embodiment, the adapters 406, 407, and 416 may be connected to one or more I/O buses that are connected to the system bus 402 via an intermediate bus bridge (not shown). Suitable I/O buses for connecting peripheral devices such as hard disk controllers, network adapters, and graphics adapters typically include common protocols, such as the Peripheral Component Interconnect (PCI). Additional input/output devices are shown as connected to the system bus 402 via an interface adapter 420 and the display adapter 416. A keyboard, a mouse, a speaker, etc. can be interconnected to the system bus 402 via the interface adapter 420, which may include, for example, a Super I/O chip integrating multiple device adapters into a single integrated circuit.

Thus, as configured in FIG. 4, the system 400 includes processing capability in the form of the processors 401, and, storage capability including the system memory 403 and the mass storage 410, input means such as the keyboard and the mouse, and output capability including the speaker and the display 415. In one embodiment, a portion of the system memory 403 and the mass storage 410 collectively store an operating system, such as the z/OS or AIX operating system from IBM Corporation, to coordinate the functions of the various components shown in FIG. 4.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

The descriptions of the various embodiments herein have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system comprising a processor and a memory storing program instructions for analyzing sentiment data corresponding to one or more users experiencing a first entertainment to generate a sentiment rating thereon, the program instructions executable by the processor to cause the system to:

transmit, by a processor and prior to the first entertainment, an incentive related to the first entertainment for providing authorization to collect physical data during the first entertainment;

receive, in exchange for the incentive related to the first entertainment, authorization to collect physical data from each user of the one or more users;

verify a presence of the one or more users at the first entertainment by connecting to a local network of a venue of the first entertainment;

collect, in response to receiving authorization, physical data procured by wearable devices corresponding to the one or more users during the first entertainment, wherein the wearable devices comprise:

one or more mobile devices in direct communication with the local network, one or more tethered devices in direct communication with the mobile device, and one or more sensors in direct communication with the local network;

receive a user review of the first entertainment from each user of the one or more users after the first entertainment has finished;

transmit, in exchange for receiving an agreement to provide the user review, an incentive related to a second entertainment to each user of the one or more users;

analyze the physical data and the user review to determine sentiment data; and generate the sentiment rating for the first entertainment based on the sentiment data, wherein the sentiment rating quantifies a collective real-time emotional response for the one or more users that experience the first entertainment.

2. The system of claim 1, wherein the physical data comprises sensor readings provided by the one or more sensors of the wearable devices that capture and identify a status of bodily functions of the one or more users.

3. The system of claim 1, wherein the program instructions are further executable by the processor to cause the system to receive one or more inputs corresponding to the one or more users indicating permission to collect the sentiment data.

4. The system of claim 1, wherein the program instructions are further executable by the processor to cause the system to detect locations with respect to the one or more mobile devices corresponding to the one or more users.

5. The system of claim 1, wherein the program instructions are further executable by the processor to cause the system to determine a local time with respect to the one or more mobile devices corresponding to the one or more users.

6. The system of claim 1, wherein the program instructions are further executable by the processor to cause the system to determine the first entertainment with respect to a location and a local time of a mobile device corresponding to a user of the one or more users.

7. The system of claim 1, wherein the sentiment data is determined from the physical data and from direct user feedback received during a time interval beginning at a conclusion of the first entertainment and extending for a predetermined amount of time.

8. A computer program product for analyzing sentiment data corresponding to one or more users experiencing a first entertainment to generate a sentiment rating, the computer program product comprising a computer readable storage medium having program instructions embodied therewith, the program instructions executable by a processor to cause the processor to:

transmit, prior to the first entertainment, an incentive related to the first entertainment for providing authorization to collect physical data during the first entertainment;

receive, in exchange for the incentive related to the first entertainment, authorization to collect physical data from each user of the one or more users;

verify a presence of the one or more users at the first entertainment by connecting to a local network of a venue of the first entertainment;

collect, in response to receiving authorization, physical data procured by one or more wearable devices corresponding to the one or more users during the first entertainment, wherein the wearable devices comprise:

one or more mobile devices in direct communication with the local network, one or more tethered devices in direct communication with the mobile device, and one or more sensors in direct communication with the local network;

receive a user review of the first entertainment from each user of the one or more users after the first entertainment has finished;

transmit, in exchange for receiving an agreement to provide the user review, an incentive related to a second entertainment to each user of the one or more users;

analyze the physical data and the user review to determine sentiment data; and generate the sentiment rating for the first entertainment based on the sentiment data, wherein the sentiment rating quantifies a collective real-time emotional response for the one or more users that experience the first entertainment.

9. The computer program product of claim 8, wherein the physical data comprises sensor readings provided by sensors of the one or more wearable devices that capture and identify a status of bodily functions of the one or more users.

10. The computer program product of claim 8, wherein the program instructions are further executable by the processor to cause the processor to receive one or more inputs corresponding to the one or more users indicating permission to collect the sentiment data.

11. The computer program product of claim 8, wherein the program instructions are further executable by the processor to cause the processor to detect locations with respect to the one or more mobile devices corresponding to the one or more users.

12. The computer program product of claim 8, wherein the program instructions are further executable by the processor to cause the processor to determine a local time with respect to the one or more mobile devices corresponding to the one or more users.

13. The computer program product of claim 8, wherein the program instructions are further executable by the processor to cause the processor to determine the first entertainment with respect to a location and a local time of a mobile device corresponding to a user of the one or more users.

* * * * *